(12) United States Patent
Halford et al.

(10) Patent No.: US 8,470,377 B2
(45) Date of Patent: Jun. 25, 2013

(54) COMPOSITION AND METHOD FOR REDUCING FOOD INTAKE

(75) Inventors: Jason C. G. Halford, Manchester (GB); Trevor R. Jarman, Haslingfield (GB)

(73) Assignee: Natures Remedies Ltd., Cambridge (GB)

( * ) Notice: Subject to any disclaimer, the term of this patent is extended or adjusted under 35 U.S.C. 154(b) by 0 days.

(21) Appl. No.: 13/380,099

(22) PCT Filed: Jun. 28, 2010

(86) PCT No.: PCT/IB2010/001722
§ 371 (c)(1),
(2), (4) Date: Jan. 25, 2012

(87) PCT Pub. No.: WO2011/001283
PCT Pub. Date: Jan. 6, 2011

(65) Prior Publication Data
US 2012/0121735 A1    May 17, 2012

Related U.S. Application Data

(60) Provisional application No. 61/222,141, filed on Jul. 1, 2009.

(51) Int. Cl.
*A01N 65/00* (2009.01)

(52) U.S. Cl.
USPC ....................................................... 424/725

(58) Field of Classification Search
None
See application file for complete search history.

(56) References Cited

U.S. PATENT DOCUMENTS

| 5,945,107 | A | 8/1999 | Hessel et al. |
| 2004/0087514 | A1 | 5/2004 | Hughes et al. |
| 2004/0198754 | A1 | 10/2004 | McKee et al. |
| 2006/0083795 | A1 | 4/2006 | Shatkina et al. |
| 2006/0228412 | A1 | 10/2006 | Clouatre et al. |
| 2008/0305096 | A1 | 12/2008 | Verdegem et al. |

FOREIGN PATENT DOCUMENTS

| AU | 2006100120 A4 | 2/2006 | |
| WO | WO 99/29332 | * | 6/1999 |
| WO | WO 2004/082609 A2 | 9/2004 | |
| WO | WO 2005/034650 A1 | 4/2005 | |

OTHER PUBLICATIONS

International Search Report from PCT/IB2010/001722, Mar. 28, 2011.
Andersen, T. and Fogh, J. "Weight Loss and Delayed Gastric Emptying Following a South American Herbal Preparation in Overweight Patients" Journal of Human Nutrition and Dietetics 2001 vol. 14:243-250.
Bosch et al. "The Effects of Dietary Fibre Type on Satiety-Related Hormones and Voluntary Food Intake in Dogs" British Journal of Nutrition 2009 vol. 102:318-325.
Mason, P. "(1) OTC Weight Control Products" The Pharmaceutical Journal 2002 269 (7206):103-105.
Ruxton, C.H.S. "Efficacy of Zotrim: a Herbal Weight Loss Preparation" Nutrition and Food Science 2004 vol. 34 (1):25-28.
Ruxton, C.H.S. and Gardner, E.J. "A Review of the Efficacy and Safety of Key Ingredients of Over-the-Counter Products for Weight Management" British Food Journal 2006 vol. 107(2):111-125.
Ruxton et al. "Effects of an Over-the-Counter Herbal Weight Management Product (Zotrim®) on Weight and Waist Circumference in a Sample of Overweight Women: a Consumer Study" Nutrition and Food Science 2005 vol. 35(5):303-314.
Ruxton et al. "Effectiveness of a Herbal Supplement (Zotrim®) for Weight Management" British Food Journal 2007 vol. 109(6):416-428.
Vinik, A.I. and Jenkins, D.J. "Dietary Fiber in Management of Diabetes" Diabetes Care 1988 vol. 11(2):160-173.
Office Communication dated Nov. 10, 2011 from U.S. Appl. No. 12/824,509, filed Jun. 28, 2010.

* cited by examiner

*Primary Examiner* — Michael Meller
(74) *Attorney, Agent, or Firm* — Licata & Tyrrell P.C.

(57) ABSTRACT

The present invention features compositions and methods for suppressing appetite. The compositions of the invention are composed of a dietary fiber and a combination of selected herbal extracts, at least one of which is capable of inhibiting gastric emptying and one which increases metabolic rate.

5 Claims, No Drawings

COMPOSITION AND METHOD FOR REDUCING FOOD INTAKE

INTRODUCTION

This application is a U.S. National Stage application of PCT/IB2010/001722 filed Jun. 28, 2010 and claims the benefit of priority of U.S. Provisional Application No. 61/222,141, filed Jul. 1, 2009, the contents of each of which are incorporated herein by reference in their entirety.

BACKGROUND OF THE INVENTION

The necessary condition for the reduction of body mass is a negative energy balance. Energy intake must be consistently lower than energy expenditure in order for weight loss to occur. Therefore, any weight control strategy must address one or both parts of the energy equation; intake or expenditure. With regard to the control of energy intake, two broad strategies can be adopted: the enhancement of the satiety response to food or the blockade of absorption. The physical and chemical properties of various foods can be used to achieve both effects.

With specific regard to the modulation of appetite, those processes responsible for the termination of a meal and the suppression of subsequent intake are of particular interest. The within meal processes of satiation and the post-meal end state of satiety are generated by the sensory, physical and chemical characteristics of the food consumed. The strength of these signals determines meal duration and meal size, and the length of the post-meal interval before the next eating occasion. The activation of such signals can be employed to enhance the appetite response to food and limit caloric intake.

Various naturally occurring ingredients including herbal extracts have been shown to produce beneficial effects on appetite and weight control when used as supplements or food components (Ruxton, et al. (2005) *Br. Food J.* 107:111-125; Ruxton, et al. (2007) *Br. Food J.* 109: 416-428). ZOTRIM is a mixed herbal preparation containing Yerbe Maté, Guarana and Damiana, common ingredients of commercially available drinks, and the product is available in the UK as a food supplement. This herb extract formulation significantly delays gastric emptying, reduced the time to perceived gastric fullness and induced significant weight loss over 45 days in overweight patients (Anderson & Fogh (2001) *J. Hum. Nutr. Dietet.* 14:243-250). A consumer study has also been undertaken to test the efficacy of this preparation in the field. A total of 48 free-living subjects completed a 28-day trial and demonstrated a self-reported mean weight loss of 2.3 kg. Questionnaire data suggested that subjects ate less at meals and snacked less frequently (Ruxton (2004) *Nutr. Food Sci.* 34:25-28; Ruxton, et al. (2005) *Nut. Food Sci.* 35:303-331; Ruxton, et al. (2007) supra). However, the effects of ZOTRIM on human food intake, feeding behaviour and subjective feelings of appetite and satiety were not determined.

FIBRESURE is a 100% natural fiber supplement that can be taken daily. The term fiber covers a wide variety of substances belonging to the family of carbohydrates that resist hydrolysis by human alimentary enzymes but are fermented by colonic micro flora (Bianchi & Capurso (2002) *Dig. Liver Dis.* 34(Suppl 2):S129-33). Fiber is normally connected with increases in satiety due to its high viscosity and bulking effect (Burton-Freeman (2000) *J. Nutr.* 130:272 S-275S). However, FIBRESURE is a fiber product with little effect on viscosity. Current recommendations for the management of obesity and diabetes mellitus include an increase in dietary fiber intake, as it may contribute to lower fasting and postprandial plasma glucose concentrations and improvement of glycaemic control, which can help control energy intake (Vinik & Jenkins (1988) *Diabetes Care* 11:160-173). FIBRESURE contains the soluble fiber inulin, which is a prebiotic carbohydrate derived from chicory root. Inulin and inulin-type fructans are mostly oligosaccharides or oligofructoses and stimulate colonic production of Short Chain Fatty Acids (SCFAs), (Guarner (2005) *Brit. J. Nutr.* 93:S61-5). Fiber fermentability which produces SCFA has been linked with increasing satiety (Bosch (2008) *Br. J. Nutr.* 102:318-325).

The mechanism by which inulin and inulin-type fructans exert a satiating effect has not been identified. There are many gastrointestinal peptides that affect food intake such as ghrelin, cholecystokinin (CCK), glucagon-like peptide-1 (7-36) amide (GLP-1), oxyntomodulin, peptide YY (PYY) and pancreatic polypeptide (PP). Fructans modulate gastrointestinal peptides involved in the control of food intake, particularly GLP-1 and ghrelin (Orskov, et al. (1989) *J. Biol. Chem.* 264(22):12826-12829). GLP-1 is an anorectic peptide secreted by the L-cells which suppresses meal-induced gastric acid and pancreatic juice secretion and slows gastric emptying (Schjoldager, et al. (1989) *Dig. Dis. Sci.* 34:703-708). There are several studies showing that peripheral injection of GLP-1 decreases food intake and consequently body weight in rats and human subjects, (Meier, et al. (2002) *Eur. J. Pharmacol.* 440:269-279; Zander, et al. (2002) *Lancet* 359:824-830). Ghrelin is associated with the mesolimbic cholinergic dopaminergic reward system. This reward link is composed of cholinergic input from the laterodorsal tegmental area to the mesolimbic dopamine system that originates in the ventral tegmental area and projects to the nucleus accumbens (Jerlhag, et al. (2007) *Addict. Biol.* 12(1):6-16). In this respect, treatment of human volunteers with approximately 20 g of oligofructose per day for 7 days increased serum GLP-1 levels (Piche, et al. (2003) *Gastroenterology* 124(4): 894-902). Furthermore, in a study of 14 healthy volunteers, it was found that the gut peptide GLP-1 decreases motility in the antro-duodeno-jejunal region thus inducing satiety (Helistrom, et al. (2008) *Neurogastroenterol. Motil.* 20(6):649-59).

SUMMARY OF THE INVENTION

The present invention features a composition for suppressing appetite, said composition being composed of a dietary fiber and a combination of selected herbal extracts wherein said combination includes at least one herbal extract capable of inhibiting gastric emptying and one herbal extract which increases metabolic rate. In one embodiment, the herbal extract which increases metabolic rate contains caffeine. In another embodiment, the at least one herbal extract capable of modifying metabolic rate achieves said effect through the presence of significant concentrations of caffeine. In other embodiments, the herbal extract which contains caffeine is Guarana, Paraguay or Kola. In particular embodiments, the herbal extracts are selected from Buchu, Vervain, Damiana, Guarana, Paraguay, Kola and Ginseng. Specifically, the present invention features a composition containing the combination of selected herbal extracts including Guarana, Damiana and Paraguay, e.g., at a ratio of 2.6:1:3.1, or when based on weight, the proportion is Guarana 95:Damiana 36:Paraguay 112. In yet other embodiments, the dietary fiber is fermentable and is selected from the group of inulin, a beta-glucan (e.g., isolated from oat bran, whole oats, oatrim or rolled oats), a pectin, a natural gum (e.g., xanthan gum, acacia gum or guar gum), an oligosaccharide (e.g., fructooligosaccharide), psyllium seed husk, a resistant dextrin, or any combination thereof.

The present invention also features a method for reducing food intake by administering to a subject in need thereof an effective amount of a dietary fiber and a combination of selected herbal extracts wherein said combination comprises at least one herbal extract capable of inhibiting gastric emptying and one herbal extract which increases metabolic rate, thereby suppressing the subject's food intake. In certain embodiments, the combination of selected herbal extracts includes Guarana, Damiana and Paraguay and the dietary fiber is fermentable.

DETAILED DESCRIPTION OF THE INVENTION

The periodic discharge of food from the stomach into the small intestine, also referred to as gastric emptying, is caused by contraction of the muscles in the wall of the stomach. These muscles are innervated by the cranial vagus nerves, which stimulate contraction of the gastric muscles and allow sphincter between the stomach and the duodenum to open. The present invention relates to a composition comprising a combination of selected herbal extracts wherein at least one of the herbal extracts inhibits gastric emptying. Because nutritional uptake through the mucosal lining of the stomach is extremely low, the extended retention period in the stomach of food resulting from these compositions does not have any discernable effect on the eventual uptake of nutrients. However, inhibition of gastric emptying results in a decreased appetite thereby decreasing food intake. As an additional feature, the compositions of the present invention further include at least one herbal extract capable of modifying metabolic rate through the presence of significant concentrations of caffeine. Increasing the metabolic rate of a patient while inhibiting gastric emptying in the patient by administering a composition of the present invention results in weight loss. Active ingredients extracted from plants are used as a natural nutritional supplement in such a way to control the uptake of nutrients by delaying gastric emptying. At the same time, plant extracts are incorporated which are known to promote weight loss by increasing metabolism. The composition of the present invention thus provides a combination of selected herbal extracts which has been shown to be effective in producing weight loss in clinical studies.

Herbal plant extracts that have been assessed and found to be suitable for selection and incorporation into a composition of the present invention for achieving a controlled and durable weight loss include Buchu (*Barosma betulina, B. crenulata, B. serratifolia*), Vervain (*Verbena officinales, V. jamaicensis, V. lappulacae, V. hesitate, V. urticifolia, V. Sinuata*), Damiana (*Tumera diffusa* var. *aphrodisiaca, T. opifera, T. ulmifoliei*), Guarana (*Paullinia cupana, P. sorbalis*), Paraguay (*Ilex paraguarensis, I. vomitora, I. Dahoon*), Kola (*Cola nitida, C. vera*), and Ginseng (*Panax ginseng, P. quinquefolius* L.). The active ingredients of each herbal extract are desirably as follows: extracts from the leaves of Buchu containing diosphenol (buchu camphor); extracts from the leaves or flowers of Vervain containing glycosides (e.g., verbanaline), adenosine, essential oils, tannin, livertin and/or emulin; Damiana extract containing ethers, terpenes (a-pinene, cineol, p-cymol, sesquiterpenes), resin, bitter pineapple, tannin, caoutchouc, albuminoids, starch, arbutin; extracts of Kola nut containing caffeine; Guarana extract containing caffeine and other xanthines (tetramethylxanthine, theobromine, theophylline, tannin); Paraguay extract containing caffeine; or extracts from the leaves or flowers of Ginseng containing triterpenoid saponins.

As those skilled in the art will appreciate, other herbal extracts having these active ingredients can also be selected for use in a composition of the present invention. In particular embodiments, an herbal extract which increases metabolic rate is specifically selected to contain caffeine. In specific embodiments, the herbal extract which increases metabolic rate does so through the presence of significant concentrations of caffeine. As described herein herbal extracts containing caffeine include, but are not limited to, Guarana, Paraguay (also referred to herein as yerbe maté) and Kola. Herbal extracts for combination into a composition of the present invention are obtained in accordance with methods described herein and those well-known and routine to those of skill in the art.

In particular, it has now been found that a combination of selected herbal extracts (e.g., yerbe mate extract, guarana extract, damiana extract) and dietary fiber can significantly decrease food intake compared to use of the herbal extracts alone or dietary fiber alone. Specifically, the combination of herbal extract and dietary fiber described herein provided a significant reduction in gram (91.4 g, 24.3%) and kcal intake (202.kcal, 26.7%) as compared to placebo-water. Further, the combined administration of herbal extract and dietary fiber produced a significant reduction in gram intake compared to placebo in all food groups except low fat sweet items; intake of high fat savory items was reduced by 18.5 g (27.6%), low fat savory intake reduced by 19.1 g (13.6%) and the greatest reductions were seen for high fat sweet items where intake was reduced by 31.1 g (48.8%). The study herein demonstrated a significant and robust effect on food intake of a standard ad libitum lunch. Accordingly, in particular embodiments, the present invention features a composition composed of a dietary fiber and a combination of selected herbal extracts which inhibit gastric emptying and increase metabolic rate for use in reducing food consumption and/or calorie intake.

As is conventional in the art, appetite is a natural desire, or longing for food. According to the present invention, increased appetite generally leads to increased feeding behavior. In this respect, an appetite suppressant is a composition that decreases the desire for food, as evidenced by a decrease in food consumption and/or calorie intake.

In accordance with one embodiment, the composition of the present invention is composed of soluble extracts of yerbe maté (leaves of *Ilex paraguayensis, I. vomitora*, or *I. dahoon*), guarana (seeds of *Paullinia cupana* or *P. sorbalis*) and damiana (leaves of *Turnera diffusa* var. *aphrodisiaca, T. opifera*, or *T. ulmifoliei*). Soluble extracts of the invention can be prepared by conventional methods of drying and/or grinding plant biomass and subjecting the same to one or more suitable solvents, thereby providing an extract, which may be either used as a crude extract or further fractionated.

Suitable methods for drying plant biomass include: sun drying followed by a heated air-drying or freeze-drying; lyophilization or chopping the biomass into small pieces, e.g., 2-10 cm, followed by heated air-drying or freeze-drying. Once sufficient moisture has been removed, e.g., more than 90%, the material can be ground to a coarse particle size, e.g., 0.01-1 mm, using a commercial grinder. For laboratory scale extraction, a coffee grinder or equivalent can be used.

In general terms, a suitable method for preparing an extract of plant biomass includes the steps of treating collected plant biomass with a solvent to extract a fraction having appetite suppressant or curbing activity, separating the extraction solution from the rest of the plant biomass, removing the solvent from the extraction solution and recovering the extract. The extract so recovered may be further purified by way of suitable extraction or purification procedures.

More specifically, plant biomass can be ground to a coarse powder as described above. Subsequently, a suitable solvent, e.g., a food grade solvent, can be added to the powder. A good grade solvent is any solvent which is suitable and approved for use in conjunction with foods intended for human consumption. Examples of suitable solvents are alcohol-based solvents, ethyl acetate, liquid carbon dioxide, hexane, and one or more components of fusel oil, e.g., ethyl acetate. Alcohol-based solvents, i.e., pure alcohol solvents and mixtures thereof with water or other organic solvents, are most desirable.

The extraction solution can then be separated from the residual plant biomass by an appropriate separation procedure such as filtration and/or centrifugation. The solvent can be removed, e.g., by means of a rotary evaporator. The separated crude extract can then be tested to confirm appetite suppressant or appetite curbing activity in a suitable in vivo bioassay.

A suitable and accepted in vivo model for measuring appetite suppression or appetite curbing activity in an animal model is described in Example 2. A clinically effective and medically approved anti-obesity drug, e.g., sibutramine, can be used as a positive control for reduction in food intake in this model. Positive results from this test model are an indicator of clinical efficacy in the human context. Alternatively, suppression, reduction or curbing of appetite can be assessed by any of the methods referred to in WO 98/46243.

Plant extracts of the invention can be dried to remove moisture, e.g., by spray-drying, freeze-drying or vacuum-drying, to yield a free-flowing powder. Optionally, the extracts can be dried on a pharmaceutically acceptable carrier, such as maltodextrin or starch. As yet a further alternative, plant biomass can be extracted and concentrated without drying to give a liquid extract, which is effective in curbing or suppressing appetite.

As described herein, other herbal extracts can be used to produce weight loss in a subject through inhibition of gastric emptying and an increase in metabolic rate. Therefore, in addition to yerbe maté, guarana and damiana extract, the composition of the invention can further include extracts from one or more of Buchu, Vervain, Kola nut, and Ginseng.

As indicated, the instant composition also features a dietary fiber. As used herein, dietary fiber is the indigestible portion of plant foods that pushes food through the digestive system and absorbs water. Dietary fiber can be soluble (able to dissolve in water) or insoluble (not able to dissolve in water). Soluble fiber, like all fiber, cannot be digested. But it does change as it passes through the digestive tract, being transformed or fermented by bacteria therein. In contrast, insoluble fiber passes through the body largely unchanged. Accordingly, in particular embodiments of the present invention, the dietary fiber is fermentable or soluble.

Fermentable dietary fiber can be obtained from a variety of plant foods, including, but not limited to legumes (e.g., peas, soybeans, and other beans); grains such as oats, rye, chia, and barley; some fruits and fruit juices including prune juice, plums, berries, bananas, and the insides of apples and pears; certain vegetables such as broccoli, carrots and Jerusalem artichokes; root vegetables such as potatoes, sweet potatoes, and onions; and psyllium seed husk. In particular embodiments, the dietary fiber is isolated and/or substantially purified to homogeneity, e.g., at least to 75%, 80%, 85%, or 90%, homogeneity or up to 99% homogeneity.

For use in accordance with the present invention, the isolated, fermentable dietary fiber is inulin, a beta-glucan, a pectin, a natural gum, an oligosaccharide, psyllium seed husk, a resistant dextrin, an alginate or a combination thereof. Inulin, belonging to the class of fibers known as fructans, is typically extracted from enriched plant sources such as chicory roots or Jerusalem artichokes. Beta-glucans, polysaccharides of D-glucose monomers linked by glycosidic bonds, are typically isolated from oat bran, whole oats, oatrim or rolled oats. Pectins, a complex set of polysaccharides that are present in most primary cell walls and particularly abundant in the non-woody parts of terrestrial plants, are composed of a linear chain of $\alpha$-(1-4)-linked D-galacturonic acid that forms the pectin-backbone. Natural gums, which are polysaccharides of natural origin that are capable of causing a large viscosity increase in solution, include, but are not limited to xanthan gum, acacia gum or guar gum. Alginate is a soluble fiber extracted from seaweed. According to the present invention, oligosaccharides, saccharide polymers containing a small number (typically three to ten) of component sugars (also known as simple sugars), particularly include fructooligosaccharides. As is conventional in the art, a resistant dextrin is a water-soluble dietary fiber obtained by, e.g., subjecting starch to high-temperature heating and enzymatic hydrolysis with $\alpha$-amylase and glucoamylase. The selection of the dietary fiber to be used in the composition of the present invention can be dependent upon the form of the composition and the manner in which the formulation is administered, e.g., as multiple different formulations or as one formulation containing yerbe maté extract, guarana extract, damiana extract and dietary fiber. In particular embodiments, the dietary fiber of the instant composition is inulin.

According to this invention, the herbal extracts and dietary fiber can be provided as a composition prepared as individual formulations (e.g., the composition includes or comprises a formulation containing yerbe maté extract, a formulation containing guarana extract, a formulation containing damiana extract, and a formulation containing a dietary fiber), or the composition can be prepared as a combination of formulations (e.g., the composition includes or comprises a formulation containing yerbe maté extract, guarana extract, and damiana extract; and a formulation containing a dietary fiber), or the composition can be prepared as a single unitary formulation (e.g., the composition includes or comprises a formulation containing yerbe maté extract, guarana extract, damiana extract, and dietary fiber). Moreover, when the composition is prepared as individual or a combination of formulations, said formulations can be the same, e.g., all tablets; or different, e.g., a capsule formulation and a liquid formulation. In addition, when taken as individual formulations, said formulations can be taken simultaneously or consecutively, e.g., within minutes of each other.

Soluble plant extracts, dietary fiber or a combination thereof can be admixed by conventional compounding procedures with any conventional pharmaceutical or nutritionally acceptable excipient, diluent or carrier in the preparation of pharmaceuticals, nutraceuticals, nutritional compositions, such as dietary supplements, slimming compositions, medical nutrition or functional foods. Typically, this involves mixing the active ingredients of the invention together with edible pharmaceutically or nutritionally acceptable solid or liquid carriers and/or excipients, e.g., fillers, such as cellulose, lactose, sucrose, mannitol, sorbitol, and calcium phosphates; and binders, such as starch, gelatin, tragacanth, methylcellulose and/or polyvinylpyrrolidone (PVP). Optional additives include lubricants and flow conditioners, e.g., silicic acid, silicon dioxide, talc, stearic acid, magnesium/calcium stearates and polyethylene glycol (PEG) diluents; disintegrating agents, e.g., starch, carboxymethyl starch, cross-linked PVP, agar, alginic acid and alginates, coloring agents, flavoring agents and melting agents. Dyes or pigments may be added to tablets or dragee coatings, for example, for identification purposes or to indicate different doses of active ingredient.

The composition of the invention can optionally include conventional food additives, such as any of emulsifiers, stabilizers, sweeteners, flavorings, coloring agents, preservatives, chelating agents, osmotic agents, buffers or agents for pH adjustment, acidulants, thickeners, texturizers and the like.

Suitable product formulations according to the present invention include sachets, soft gel, powders, syrups, pills, capsules, tablets, liquid drops, sublinguals, patches, suppositories, and liquids. Also contemplated are food and beverage products containing the composition of the present invention, such as solid food products, like bars (e.g., nutritional bars or cereal bars), powdered drinks, dairy products, breakfast cereals, muesli, candies, confectioneries, cookies, biscuits, crackers, chocolate, chewing-gum, desserts and the like; liquid comestibles, like soft drinks, juice, sports drinks, milk drinks, milk-shakes, yogurt drinks or soups, as well as pet treats, pet foods, etc.

The composition of the invention can be provided as a component of a normal meal, e.g., a nutritional or slimming composition, or dietary supplement, in the form of a health drink, a snack or a nutritionally fortified beverage, as well as a pill, a tablet or a softgel, for example. When used as a snack or dietary supplement it will preferably be consumed between or before meals.

Optionally, the composition according to the invention can be nutritionally complete, i.e., may include vitamins, minerals, trace elements as well as nitrogen, carbohydrate and fatty acid sources so that it may be used as the sole source of nutrition supplying essentially all the required daily amounts of vitamins, minerals, carbohydrates, fatty acids, proteins and the like. Accordingly, the composition of the invention may be provided in the form of a nutritionally balanced complete meal, e.g., suited for oral or tube feeding.

In addition to the herbal extracts and dietary fiber, the composition of the invention may also include one or more further active ingredients, e.g., capsaicin (red pepper); fatty acids, especially linoleic acid (LA) and conjugated linoleic acid (CLA); glycomacropeptide (GMP); Long Chain Triglyceride (LCT); enterostatin; galactose; glucuronic acid; hydroxycitrate (HCA); citrus; β-hydroxy butyrate; medium chain tryglycerides (MCTs); D-tagatose; caffeine; potato extract; green tea extract; epigallocatechin gallate, or other catechins; peptide D4; vitamins B, C and/or E; and chromium picolinate. Alternatively, the composition of the invention may be combined with an anti-obesity drug, such as sibutramine. For example, the composition of the invention may be provided in the form of a kit for separate, sequential or simultaneous administration in conjunction with an anti-obesity drug such as orlistat (XENICAL™), Hoodia extract, and the like.

Daily dosage of a composition of the present invention would usually be single or multiple servings per day, e.g., once or twice daily, for acute or chronic use. However, benefit may be derived from dosing regimens that can include consumption on a daily, weekly or monthly basis or any combination thereof. Administration of compositions of the invention, e.g., treatment, could continue over a period of days, weeks, months or years, in order, for example, to constantly control the weight, or until a healthy or cosmetically beneficial loss of body weight has occurred. Optimally, the composition of the invention is consumed at least once a day on a regular basis, prior to (i.e., pre-prandial administration), or during a meal. Preferably, the composition of the invention is consumed prior to a meal.

The amount and dosage regimen of the composition of the invention to be administered is determined in the light of various relevant factors including the purpose of administration, the age, sex and body weight of an individual subject, i.e., inter alia on the severity of the subject's obesity or overweight. In this respect, the compositions of the invention can be administered under the supervision of a medical specialist, or may be self-administered.

Preferred delivery formats for the appetite suppressing or appetite curbing composition of the invention, would be as a dietary supplement containing about 50 mg to about 150 mg, or preferably about 100 mg to about 120 mg, dry weight of yerbe maté extract; about 50 mg to about 120 mg, or preferably about 90 mg to 100 mg, of gaurana extract; about 20 mg to about 50 mg, or preferably about 30 mg to about 40 mg, of damiana extract; and about 2 grams to about 10 grams, or preferably about 5 grams to 7 grams, of dietary fiber. In specific embodiments, the herbal extracts are, by weight, used at a ratio of Guarana 95:Damiana 36:Paraguay 112. Alternatively, the ratio of Guarana:Damiana:Paraguay is 2.6:1:3.1.

An illustrative example of a formulation of herbal extracts is 27.5% weight yerbe maté extract, 23.2% weight Guarana, 9% weight Damiana extract, and 40.3% weight of dicalcium phosphate, talc, sodium carboxymethylcellulose, magnesium stearate and hydroxypropylmethylcellulose as additional ingredients.

The present invention also features a method for decrease food intake and/or suppressing appetite by administering to a subject in need thereof an effective amount of yerbe maté extract, guarana extract, and damiana extract in combination with a dietary fiber. Administration of the composition of the present invention results in a 10% to 40% decrease in food consumption (gram weight) or a 10% to 35% decrease in calorie intake (Kcal) as compared to a subject not receiving the composition. In particular embodiments, the composition of the present invention achieves a 20 to 30% reduction in food consumption or calorie intake, levels which unexpectedly surpass other nutritional weight loss compositions. For example, while humans studies analyzing the effects of *Caralluma fimbriata* have shown a 8.2% reduction in energy intake (Kuriyan, et al. (2007) *Appetite* 48:338-344), human studies of sodium alginate showed a 7% reduction in energy intake (Paxman, et al. (2008) Appetite 51:713-719), human studies of oligofructose (soluble fermentable non-viscous fiber) have shown a 5% reduction in total intake (Cani, et al. (2006) *Euro. J. Clin. Nutr.* 60:567-572), and human studies of hydroxycitric acid (HCA-SX) and a combination of HCA-SX and niacin-bound chromium (NBC) and *Gymnema sylvestre* extract (GSE) have shown a 4% decrease in food intake (Preuss, et al. (2004) *Nutr. Res.* 24:45-58), human studies with a natural dietary compound of chromium picolinate, inulin, capsicum, L-phenylalanine, and other lipotropic nutrients has not shown any significant difference in energy intake (Hoeger, et al. (1998) *Adv. Ther.* 15:305-14). Similarly, food intake and appetite ratings were not significantly reduced when either beta-glucan and fructooligosaccharides are used alone or in combination (Peters, et al. (2009) *Am. J. Clin. Nutr.* 89:58-63; Kim, et al. (2006) *Cer. Foods World*, pg. 29), or with a fiber system of alginate and guar gum (Mattes (2007) *Physiol. Behav.* 90:705-711), or with supplements of fermentable fibers (pectin, beta-glucan) and non-fermentable methylcellulose (Howarth, et al. (2003) *J. Nutr.* 133:3141-3144). Indeed, the levels of reduction in food/calorie intake of the instant composition are more comparable to pharmacological options including sibutramine (12-26% reduction; Rolls, et al. (1998) Obes. Res. 6:1-11; Chapelot, et al. (2000) Physiol. Behav. 68:299-308), diethylpropion (11-15% reduction; Porikos, et al. (1980) Clin. Pharmacol. Ther. 27:815-822), fluoxetin (13-16% reduction; McGuirk & Silverstone (1990) Int. J. Obes. 14:361-72) and fenfluramine/d-fenfluramine (17-22% reduction; Goodall & Silverstone (1988) Appetite 11:215-288. See, also, Halford, et al. (2007) Drugs 67:27-55 and Halford, et al. (2004) Curr. Drug Targets 5:221-40.

Subjects benefiting from the method of the invention include those in need of weight loss, e.g. overweight or obese subjects, as well as subjects controlling food intake so as not to gain weight. In some embodiments, subjects receiving the composition of this invention are average or slightly overweight, i.e., having a BMI of 18.5-29.9 kg/m$^2$. In other embodiments, subjects receiving the composition of this invention are overweight, i.e., having a BMI of greater than 29.9 kg/m$^2$. In further embodiments, subjects benefiting from the method of the invention are those that consume high fat food, e.g., food containing greater than 8 g of fat per 100 g.

In addition to the uses described therein, the invention further provides a composition according to the invention for use in suppressing appetite.

The invention additionally provides the use of yerba mate extract, guarana extract, daminiana extract and a dietary fiber in the manufacture of a composition for suppressing appetite.

The invention is described in greater detail by the following non-limiting examples.

EXAMPLE 1

Effect of Selected Herbal Extracts on Gastric Emptying and Metabolic Weight

A composition of the present invention containing a combination of selected herbal extracts was administered to patients in a double blind controlled clinical trial. The combination tested included Guarana, Damiana, and Paraguay. These extracts were obtained as powders. The components were mixed and prepared as capsules. Each capsule contained 95 mg Guarana, 112 mg Paraguay, and 36 mg Damiana extract. The subjects for the study were 20 otherwise healthy subjects, complaining of light-moderate overweight with a body mass index between 25 and 30 kg/m$^2$. None of the subjects were taking any drug or dietary supplement at the time of the study. All were briefed on the protocol and gave consent to the trial.

In this double blind placebo controlled trial, the subjects were randomized into two groups A and B. Group A was supplied with test capsules and group B with placebo (water-coated capsules containing lactose) for 20 days. The participants took three meals a day and were instructed to take 2 capsules with a large glass of water (250 ml) from 10-15 minutes before each meal. Using a stopwatch, each subject then recorded the time elapsing to perception of gastric fullness. Subjects also were asked to note any side effects. Three days after the end of the first 20 day trial, the procedure was repeated with the test capsules now being given to the group B subjects and the placebo capsules to group A subjects. All subjects completed the test.

The subjects in group B, receiving the placebo capsules in the first period reported an average time for perception of fullness of 60 minutes (range 55-65 minutes). In the second period, when taking the test combination product, the average time for perception of fullness in this same group was 36 minutes (range 33-41 minutes). These average values were statistically different (p<0.01). Therefore, the study showed that treatment with the herbal extract combination produced statistically significant decreases in the time to perception of fullness.

The rate of gastric emptying was assessed by scintigraphy. Three volunteer male subjects with no gastrointestinal illness or intake of medicinal drugs took part in the study. They were given a meal composed of 18 g peas, 100 g dried potatoes, and 200 ml of water containing 16-20 Mbc 113 Indium-DPTA. The subjects were fasting before the test and the meal was consumed in five minutes. The test was conducted with the subjects in a semi-upright position with a gamma camera placed in front. The time course of radioactivity in the stomach was determined by measuring the radioactivity in an appropriate region of interest every minute over 90 minutes. The test as repeated after each subject had taken three capsules of the drug combination three times daily and three capsules having been mixed with the food. Results showed that the rate of gastric emptying was significantly decreased in the three subjects after taking the herbal extract combination product. Halving times of gastric emptying were 49, 31, and 32 minutes after taking the test product and 61, 50, and 49 minutes, respectively, after taking the placebo.

Ultrasound examination of the stomach was also employed using a 3.5 MHz curved array transducer and an Aloka 630 standard unit employing a modification of the techniques by Holt, et al. ((1980) Gut 1:597-601) and Bateman & Whittingham ((1982) Gut 23:524-527). Continuous scans were performed switching the transducer between two alternate projections, one oblique upward view with the transducer positioned under the left curvature allowing the gastric fundus, corpus, and antrum to be inspected or a transverse view across the epigastrium with a slight upward direction viewing the antrum pylorus and the duodenal bulb. All examinations were recorded on videotape and still pictures were taken every five minutes. This technique was used in a further double-blind crossover study on seven healthy normal volunteers with no history of gastrointestinal diseases. Each volunteer had 2 to 8 examinations with the test capsules or placebo capsules (lactose), followed by 20 ml of apple juice and 15 minutes later with 400 ml of apple juice. The projections gave clear visual estimation of the volume of the stomach. Gastric emptying time (GET) was defined as the elapsed time between ingestion of the 400 ml of apple juice and the time when the fundus and corpus of the stomas were completely empty. The results were noted immediately and controlled by playback of the videotapes. After termination of the study the codes were broken and GET values were compared by an independent analyst. The results showed that there was a considerable variation among the subjects and within the same subject. However, even with this variability, a delaying effect on gastric emptying was associated with administration of the herbal extract combination product, an effect that was evident in all seven subjects and is shown in Table 1.

TABLE 1

| Subject | Placebo GET (minutes) | Herbal Extract GET (minutes) |
|---|---|---|
| A | 37.0 | 63.5 |
| B | 47.5 | 70.0 |
| E | 45.5 | 80.0 |
| M | 29.0 | 44.5 |
| H | 31.0 | 46.0 |
| J | 34.0 | 39.0 |

TABLE 1-continued

| Subject | Placebo GET (minutes) | Herbal Extract GET (minutes) |
|---|---|---|
| T | 44.0 | 60.0 |
| Mean Value | 31.8 | 57.6 |

The effect on body weight of 10 days treatment with the test compound and placebo was recorded in a double blind pilot study of 44 healthy subjects was also determined. None of the subjects took any drugs and none were on a specific diet. The patients were instructed to take three capsules (test compounds or placebo) with a large glass of water 15 minutes before main meals and also to take care to not change their normal food habits. They also were asked to note side effects. The subjects were weighed before and after the period of 10 days. Twenty-two patients with a BMI range 25.1 to 29.5 took the test capsules and 22 patients with a BMI of 24.9 to 29.0 received the placebo. Results showed that of the 22 subjects who received the placebo, there was a mean decrease in body weight of 0.3 kg (SEM=0.03) while in the 22 subjects who received the herbal extract product, there was a mean decrease of 0.8 kg (SEM=0.05).

The effect on body weight of 45 days of treatment with the herb combination and placebo was also studied in a double blind randomized crossover study of 47 patients. These subjects were healthy but overweight (BMI range 25.8 to 30.4). They did not take any medicinal drug or diet before or during the study. All 47 were between the ages of 20 and 60 years of age and gave full consent. In the study, the 24 subjects in group A received the test capsules in the first period. This group showed a mean decrease in body weight of 5.1 kg (SEM=0.5) while taking the herbal extract product. In contrast, the placebo group in the first period had a mean decrease in body weight of only 0.5 kg (SEM=0.08).

A recording of weight maintenance over 12 months after an initial weight loss was made to assess the long term effectiveness of the treatment. Twenty-two of the subjects from the various studies above who had lost an average of 3.6 kg were invited to take part. Each subject received a month's supply of the test drug each month they returned to the study center for weight measurement.

No side effects were noted in any of the clinical tests. The results of these experiments demonstrate the effectiveness of the herbal extract combination in weight reduction in humans.

EXAMPLE 2

Effect of Selected Herbal Extracts in Combination with Dietary Fiber

Study Design. This was a double-blind, placebo-controlled study using a randomized within-subject design to evaluate the effects of ZOTRIM and inulin fiber given together, separately and against placebo control in terms of food intake in grams and kilocalories and subsequent food ratings measured using visual analogue scales (VAS) of hunger, fullness, prospective consumption, desire to eat and satisfaction pre dosing, pre and post meals and at hourly intervals across the day. The independent variables were the four conditions—ZOTRIM (tablet form) and inulin fiber (powder mixed with water), ZOTRIM and control, inulin fiber and placebo and control and placebo. The dependant variables were food intake measured in grams, kilocalories and macronutrients and the VAS ratings. All food and water was recorded by weight scales (Sartorius Model CPA 4202S, Sartorius Ltd, Epsom, UK; 0.1 gram accuracy) before and after meals to ascertain intake in grams, kilocalories and macronutrients, and food choice. There were two VAS's: the first was given nine times throughout the study day and measured hunger, fullness, prospective consumption, desire to eat, satisfaction, nausea and thirst. The second VAS measured pleasantness, palatability, tastiness, saltiness and sweetness and was given after breakfast and lunch. The product/placebo was administered 15 minutes before breakfast and lunch which were four hours apart. Participants were randomized to the study by means of a block plan created on an internet-based randomization program.

Participants. Fifty-eight healthy, average and slightly overweight (body mass index [BMI]: 18.5-29.9 kg/m$^2$) women completed the study. Volunteers were recruited by advertisement. Upon response to the advertisements, individuals completed a standardized telephone or email interview to assess their age, height, weight, occupation, smoking status and ability to attend the study center at the requisite times. Those who were aged over 65, with a BMI<18.5 kg/m$^2$ or >29.9 kg/m$^2$, who disliked more than 25% of the ad-libitum lunch study foods, were smokers, currently dieting, or who did not eat regular meals, were not studied further.

Initial Screening. Following the initial telephone/email interview, potential participants received detailed information on the protocol, and were invited to the study center, (The Kissileff Laboratory for the Study of Ingestive Behaviour in the School of Psychology, The University of Liverpool), for a full screening no more than 21 days before commencing the study. All volunteers signed an informed consent before any study-specific procedures were undertaken. Confidentiality and anonymity were assured.

At screening, the following measurements were taken: height measured without shoes, using a stadiometer to the nearest cm and weight using standard calibrated scales to the nearest 0.1 kg. Participants also completed a medical history, diet history, and eating behavior questionnaire (The Dutch Eating Behaviour Questionnaire [DEBQ-R]).

Exclusion Criteria. Following screening, participants were excluded from the study if they reported any of the following: significant health problems; not having dieted in the last 12 months to lose or control weight; currently adhering to a specific food avoidance diet; gastrointestinal symptoms requiring treatment; bariatric surgery; systemic or local treatment likely to interfere with evaluation of the study parameters; taking medication known to affect appetite or weight within the past month and/or during the study; pregnant or planning to become pregnant or breastfeeding; history of anaphylaxis to food; general or specific food allergies, including caffeine and any of the study foods; dislike of more than 25% of the ad-libitum study foods; extreme dietary restraint; non breakfast eaters; working in nutrition, dietetics, food research, food manufacturing or supplements industry.

Those participants who fulfilled the study criteria were recruited to the study and assigned a code number.

Study Supplement. The ZOTRIM formulation contained 112 mg Yerbe Mate, 95 mg Guarana and 36 mg Damiana. Guarana, a dough made from the seeds of *Paullinia cupana*, which grows in Brazil and Venezuela, contains 3-6% caffeine, 5-8.5% tannins, 7.8% resins, 2-3% lipid, 0.06% saponin, 5-6% starch and 1.5% coloring agents (Schery (1954) *Plants for Man*. London: George Allen and Unwin, pp. 518-519). Yerbe Maté is an extract of *Ilex paraguayensis* from Brazil, Argentina and Paraguay containing 1-1.5% caffeine, 4-10% tannins and 3% resins and lipids (Hill (1952) *Economic Botany*. New York: McGraw-Hill Book Company, pp. 479-

481.). Damiana is obtained from the leaves of the plant *Turnera diffusa* var. *aphrodisiaca* from California, Mexico, Brazil and Bolivia and contains ethereal oils, resins and tannins (Bradley (1992) *British Medical Compendium*, Vol. 1. London: British Herbal Medical Association, pp. 71-72.).

The placebo contained lactose and other ingredients minus the active ingredients. ZOTRIM and placebo were supplied as individual tablets and packaged in coded containers labeled A or B to ensure the double-blind status of the study. All capsule components (active and inert ingredients) were those approved and commonly used for commercial supplements and health ingredients and produced by a commercial capsule manufacturer. The inulin fiber (FIBRESURE) was derived from chicory root and packaged in powder form in 5.8 g individual stick packs, containing 5 g fiber per pack. Each dose of 5 grams of fiber was mixed into 100 grams of water.

Participants were instructed to take the dose of 3 tablets with a glass of water (100 g) 15 minutes before their two main meals of each day. The order of treatments was counterbalanced across the four treatment conditions, with inulin being mixed in or not mixed into the water according to condition.

Materials and Tools. VAS were used to rate degree of hunger, fullness, satisfaction, desire to eat, perception of how much participants could eat (prospective consumption), thirst and nausea. VAS was composed of 100 mm horizontal lines anchored by "not at all" and "extremely" at opposite ends, upon which participants record with a vertical line their subjective ratings. For example, hunger was rated along a 100 mm line that was preceded by the question "how hungry do you feel at this moment?" and anchored on the left by "not at all hungry" and on the right by "extremely hungry", or "how pleasant was the breakfast?" being anchored on the left by "not at all pleasant" and on the right by "extremely pleasant".

Participants completed these ratings nine times (T1-T9) during each test day. The exact times were: pre dose pre breakfast (T1), pre breakfast (T2), post breakfast (T3), Interval 1 (T4), Interval 2 (T5), Interval 3 (T6), pre dose pre lunch (T), pre lunch (T8), and post lunch (T9) Pleasantness VAS were completed at two time points, viz; post breakfast and post lunch.

Procedure. At the screening visit, participants were asked if they had read and understood the information sheet concerning the study (which they were sent a minimum of two days before the screening visit). Participants were then asked to sign two copies of the consent form. Participants' height and weight were measured. BMIs were calculated ensuring they were in a suitable range for the study. Participant's medical history and weight control history were taken. A DEBQ and list of study foods were shown to the participants to ensure that they did not have any objections or intolerances to the study foods. Following the screening, participants were contacted to determine whether or not they were able to continue in the study. Successful participants then received an information pack which contained details of their agreed times to visit the lab. Participants were asked to fill in an evening food and activity diary prior to attending the visits.

Visit two took place at a minimum of two days after screening. Subsequent visits took place as soon as possible leaving two days between visits (giving a total of four visits). Breakfast was served between 8:30 AM and 9:45 AM (time depending on when researcher and participant had arranged to meet at lab). If participants failed to attend their visit within these time limits, their session was rescheduled for another day.

The protocol for the laboratory visits (four in total) was as follows: On the day preceding each study day participants were asked to keep their food intake, fluid intake and activity levels similar and not to consume any alcohol. On each pre-study evening participants were requested to record in a diary the food and drink they consumed and the activities they undertook from 5:00 PM until they retired for the night. They were asked not to eat or drink anything except water from 12:00 midnight until they attended at the study center the following morning.

At 8:30 AM on each study day participants attended the study center. The diary was collected and participants were given instructions on completing the VAS, before filling in the first set of VAS ratings (T1). The pre-breakfast dose of product/placebo and a glass containing 100 ml water were presented to the participant 15 minutes before breakfast. They were instructed to consume all of the tablets with all of the water. They were weighed and details of compliance were recorded. Participants were then seated in the testing area in individual cubicles. After completing the pre-breakfast VAS ratings (T2), participants were given a fixed-load breakfast as shown in Table 2, and were asked to consume everything presented within 20 minutes. After breakfast, participants completed a post-breakfast set of VAS appetite (T3) and pleasantness ratings, and were then free to leave the study center. They were instructed not to eat or drink anything except water that was provided by the study. They were asked to complete VAS ratings at hourly intervals (T4, T5 and T6) and to return to the study center three three hours and forty minutes after their first dose was given to ensure their second dose would be given on time. On their return, the VAS measures and remaining water (if any) were collected for assessment and a pre-dose VAS (T7) was completed. Fifteen minutes before lunch was to be served (four hours after breakfast had been served) the study product/placebo was presented with a glass containing 100 ml water and participants were instructed to swallow all of the tablets with all of the water.

TABLE 2

| Food* | Amount (g) | | % |
|---|---|---|---|
| Kellogg's Cornflakes | 30 | | |
| Semi-skimmed UHT Milk | 125 | | |
| Orange Juice | 200 | | |
| Sliced White Bread (toasted) | 60 | % Energy from Protein | 10 |
| Flora Margarine | 10 | % Energy from Fat | 17 |
| Strawberry Jam | 20 | % Energy from Carbohydrate | 73 |
| TOTAL WEIGHT | 445 | TOTAL KCALS | 496 |

*Also included hot drink, 35 g milk and sugar if required.

A 15-minute rest period followed, during which the participants remained in the study center. They then completed another VAS (T8) and were served an ad-libitum lunch as detailed in Table 3. Participants were instructed to eat as much as they liked from the choice of foods and water offered, taking as long as they wished, and signaling when they had finished. Immediately following ad-libitum consumption of the test meal, participants completed a set of post-lunch VAS ratings (T9).

Participants were then free to leave the study center. All food and water was weighed (Sartorius Ltd) to the nearest 0.1 g before and after each meal to determine intake. The length of each meal was timed by the study staff although participants were only instructed there was a time limit (of 20 minutes) at breakfast. After completion of the study participants were debriefed and were reimbursed for their time and travel expenses (if any).

Test Meals. A standard fixed-load breakfast (496 kcal) was dispensed to participants in all conditions (Table 2). In addition to the fixed-load breakfast, at the first visit, participants were offered a hot drink of tea or coffee with additional milk (35 g) and sugar if desired. If requested, this drink had to be consumed on each subsequent visit. The amount and energy composition of the ad-libitum cold test lunch items is listed in Table 3. The protein, carbohydrate and fat content of each test lung item are respectively listed in Tables 4-6. This meal was designed to offer a selection of high and low fat savory and sweet food items. Water (500 ml) was offered at the test meal. Participants were instructed to eat as much as they wished and to signal via a booth-based buzzer when they had finished.

TABLE 3

| Food | Amount (g) | Kcal/100 g | Kcal in Serving |
|---|---|---|---|
| Tesco Medium Sliced White Bread | 144.00 | 240.00 | 345.60 |
| Flora | 40.00 | 531.00 | 212.40 |
| Tesco Sandwich Turkey | 62.50 | 110.00 | 68.75 |
| Tesco Danish Salami | 44.60 | 495.00 | 220.77 |
| Tesco Medium Grated Cheddar | 100.00 | 415.00 | 415.00 |
| Cucumber | 80.00 | 10.00 | 8.00 |
| Walkers Ready Salted Crisps | 25.00 | 530.00 | 132.50 |
| Quaker Snack-a-jacks S&V | 30.00 | 410.00 | 123.00 |
| Tesco Value Cookies | 100.00 | 515.00 | 515.00 |
| Tesco Chocolate Mousse | 62.50 | 200.00 | 125.00 |
| Tesco Value Fruit Cocktail | 410.00 | 46.00 | 188.60 |
| Tesco Jelly Babies | 120.00 | 368.00 | 441.60 |
| Total | | | 2796.22 |

TABLE 4

| Food | Protein/100 g | Protein in Serving |
|---|---|---|
| Tesco Medium Sliced White Bread | 8.20 | 11.81 |
| Flora | 0.00 | 0.00 |
| Tesco Sandwich Turkey | 21.20 | 13.25 |
| Tesco Danish Salami | 13.20 | 5.89 |
| Tesco Medium Grated Cheddar | 24.40 | 24.40 |
| Cucumber | 0.70 | 0.56 |
| Walkers Ready Salted Crisps | 6.50 | 1.63 |
| Quaker Snack-a-jacks S&V | 6.50 | 1.95 |
| Tesco Value Cookies | 4.80 | 4.80 |
| Tesco Chocolate Mousse | 3.50 | 2.19 |
| Tesco Value Fruit Cocktail | 0.40 | 1.64 |
| Tesco Jelly Babies | 2.30 | 2.76 |
| Total | | 70.87 |

TABLE 5

| Food | Carbohydrate/100 g | Carbohydrate in Serving |
|---|---|---|
| Tesco Medium Sliced White Bread | 47.80 | 68.83 |
| Flora | 0.00 | 0.00 |
| Tesco Sandwich Turkey | 0.80 | 0.50 |
| Tesco Danish Salami | 7.00 | 3.12 |
| Tesco Medium Grated Cheddar | 1.40 | 1.40 |
| Cucumber | 1.50 | 1.20 |
| Walkers Ready Salted Crisps | 49.00 | 12.25 |
| Quaker Snack-a-jacks S&V | 77.00 | 23.10 |
| Tesco Value Cookies | 65.00 | 65.00 |
| Tesco Chocolate Mousse | 26.80 | 16.75 |

TABLE 5-continued

| Food | Carbohydrate/100 g | Carbohydrate in Serving |
|---|---|---|
| Tesco Value Fruit Cocktail | 11.00 | 45.10 |
| Tesco Jelly Babies | 89.80 | 107.76 |
| Total | | 345.01 |

TABLE 6

| Food | Fat/100 g | Fat in Serving |
|---|---|---|
| Tesco Medium Sliced White Bread | 1.50 | 2.16 |
| Flora | 59.00 | 23.60 |
| Tesco Sandwich Turkey | 2.30 | 1.44 |
| Tesco Danish Salami | 46.00 | 20.52 |
| Tesco Medium Grated Cheddar | 34.40 | 34.40 |
| Cucumber | 0.10 | 0.08 |
| Walkers Ready Salted Crisps | 34.00 | 8.50 |
| Quaker Snack-a-jacks S&V | 8.00 | 2.40 |
| Tesco Value Cookies | 26.10 | 26.10 |
| Tesco Chocolate Mousse | 8.40 | 5.25 |
| Tesco Value Fruit Cocktail | 0.00 | 0.00 |
| Tesco Jelly Babies | 0.00 | 0.00 |
| Total | | 124.44 |

Lunch time was fixed at precisely 4 hours after breakfast. All meals were served in individual booths in the test study center.

Adverse Events. If participants reported any adverse events they had experienced while taking the study supplement the type, severity, date of onset and resolution were recorded.

Statistical Analysis. Analysis was performed using SPSS for WINDOWS, Version 16 (SPSS Inc., Chicago, US). Analysis of variance (ANOVA) and post-hoc paired t-tests were used. The assumptions of the ANOVA model were tested and if homogeneity of variance was not found, multivariate tests were adopted for that variable. All tests were two-tailed unless stated. Bonferroni corrections were applied for multiple comparisons.

Intake at the test meal was initially analyzed for amount consumed (in grams and kcal) using a two-way ANOVA with condition (inulin fiber and ZOTRIM) as within-subject factors. Because breakfast was fixed, this was not included in the statistical analysis. Paired t-tests were used to investigate any significant differences. This analysis was then re-run incorporating the kcal content of breakfast and the kcal content in the inulin fiber conditions. A two-way ANOVA with inulin and ZOTRIM as within subject factors was performed to analyze food choice at the test meal. Kcal intake of high and low fat savory and high and low fat sweet items were compared between conditions.

Subjective parameters (e.g., hunger, gastric fullness) rated on the VAS were analyzed using a within-subjects repeated measures ANOVA with condition (ZOTRIM and placebo) and time (pre-dose pre-breakfast, pre-breakfast, post-breakfast, 10 AM, 11 AM, 12 PM, pre-dose pre-lunch, pre-lunch, post-lunch, 2 PM, 3 PM, 4 PM, and 5 PM; T1-T13) as within-subject factors. If a time-by-condition interaction effect was found significant, paired t-tests were conducted at each rating time between conditions.

Results. Fifty-eight healthy average to slightly overweight women were recruited to the study through advertising. A double blind, placebo-controlled, cross-over design was employed. After screening, eligible participants were invited to the laboratory on four separate occasions for breakfast and lunch. The study days were arranged according to the participants' availability and always leaving a minimum of two days between each visit. On study days, the participants were administered the first dose of ZOTRIM and inulin fiber (5.8 g), ZOTRIM and water, inulin fiber and placebo or water and placebo, 15 minutes before a fixed load breakfast. Four hours after the initial dose, and 15 minutes before lunch, the second dose of the same condition was given. The dose was composed of three tablets, either ZOTRIM or a placebo, and a hundred grams of water into which inulin fiber was or was not mixed according to condition. Participants were then offered an ad-libitum buffet lunch and the intake of each item of lunch was measured. Appetite was assessed using VAS.

In total 71 participants were screened, 62 were recruited and 58 completed the study. Nine participants were excluded, six as their BMI was >29.9, two due to medication they were taking and one as her BMI was <18.5. Of the four that were recruited to the study but did not complete it, three could not fit the visits around previous commitments and one could not be contacted after her first visit. Their data has been excluded from analysis.

The demographic (age), and anthropometric (weight, height, BMI) characteristics of the completing participants are shown in Table 7.

TABLE 7

|  | Mean (±SD, n = 58) |
| --- | --- |
| Age (years) | 21.31 ± 3.79 |
| Weight (kg) | 60.16 ± 6.09 |
| Height (m) | 166.24 ± 5.23 |
| Body Mass Index (BMI) [kg/m$^2$] | 21.78 ± 1.99 |
| DEBQ | 2.56 ± 1.92 |

Intake at Test Meal. Total mean number of grams (g) and kilocalories (kcal) consumed in each condition are displayed in Table 8.

TABLE 8

|  | Number (N) | Mean Intake in Grams (g) (±SD) | Mean Intake in Kilocalories (kcal) (±SD) |
| --- | --- | --- | --- |
| Condition A (placebo) | 58 | 375.60 (±138.46) | 752.14 (±296.27) |
| Condition B (ZOTRIM) | 58 | 328.96 (±177.20) | 619.94 (±263.51) |
| Condition C (FIBRESURE) | 58 | 356.50 (±144.38) | 662.30 (±311.69) |
| Condition D (ZOTRIM and FIBRESURE) | 58 | 284.20 (±105.47) | 549.78 (±182.16) |

Gram Intake. A 2×2 repeated measures ANOVA demonstrated a significant main effect of ZOTRIM on gram intake $(F(1, 57)=26.110, p<0.001)$. The ANOVA also demonstrated a significant main effect of inulin fiber on gram intake across conditions, $(F(1, 57)=12.661, p=0.001)$. There was no interaction between ZOTRIM and fiber conditions $(F(1, 57)=1.841, p=0.180)$ on gram intake.

Paired samples t-tests showed that there was a significant reduction in gram intake from control of 46.6 grams (12.4%) in the ZOTRIM condition $(t(57)=3.254, p=0.002)$ and of 91.4 grams (24.3%) in the ZOTRIM and fiber condition combined $(t(57)=5.757, p<0.001)$. The reduction in intake of 19.1 gram (5.1%) from control in the inulin only condition compared to the control condition proved insignificant $(p=0.188)$. Intake was significantly lower in the ZOTRIM and fiber combined condition versus the ZOTRIM alone $(t(57)=3.852, p<0.001)$ or fiber alone conditions $(t(57)=4.624, p<0.001)$.

Energy Intake. A 2×2 repeated measures ANOVA demonstrated a significant main effect of ZOTRIM on caloric intake $(F(1, 57)=16.681, p<0.001)$. The ANOVA also demonstrated a significant main effect of inulin fiber on caloric intake across conditions, $(F(1, 57)=13.366, p=0.001)$. There was no interaction between ZOTRIM and fiber conditions $(F(1, 57)=0.193, p=0.662)$.

Paired samples t-tests showed there was a significant reduction in caloric intake from control of 132.2 kcal (17.6%) in the ZOTRIM condition $(t(57)=3.365, p=0.001)$, of 89.9 kcal (11.9%) in the fiber condition $(t(57)=2.621, p=0.011)$ and of 202.4 kcal (26.9%) in the ZOTRIM and inulin fiber condition combined $(t(57)=5.629, p<0.001)$. Caloric intake was significantly lower in the ZOTRIM and fiber combined condition versus the ZOTRIM alone $(t(57)=2.504, p=0.015)$ or fiber alone conditions $(t(57)=3.178, p=0.002)$.

Analysis of the time taken to consume the ad-libitum lunch revealed a significant main effect of ZOTRIM $(F(1,57)=4.196, p=0.045)$. There was no effect of inulin fiber $(F(1,57)=0.010, p=0.921)$ and no interaction between ZOTRIM and inulin fiber $(F(1,57)=3.316, p=0.074)$. Paired samples t-test showed there was a shorter lunch duration with ZOTRIM alone compared to placebo $(t(57)=2.903, p=0.005)$.

Food Choice. The twelve food items offered at the ad-libitum lunch were analyzed according to variation in fat content and taste. Foods offered were grouped into high fat savory (HFSV), low fat savory (LFSV), high fat sweet (HFSW), low fat sweet (LFSW) sets, as shown in Table 9.

TABLE 9

| HFSV | LFSV | HFSW | LFSW |
| --- | --- | --- | --- |
| flora | bread | Cookies | Jelly Babies |
| salami | turkey | Chocolate Mousse | Fruit Cocktail |
| cheese | snack a jacks |  |  |
| crisps | cucumber |  |  |

A four way within-subjects ANOVA was performed with taste (savory/sweet), fat (high/low), inulin fiber (present/not) and ZOTRIM (present/not) as within-subjects factors. Significant main effects of taste $(F(1,57)=10.457, p=0.002)$, fat $(F(1,57)=90.637, p<0.001)$, inulin fiber $(F(1,57)=9.775, p=0.003)$ and ZOTRIM $(F(1,57)=23.944, p<0.001)$ were found on intake, but there were no significant interactions (see FIG. 1). Subsequent t-tests revealed that overall, gram intake of savory items was significantly greater than intake of sweet items $(t(57)=3.234, p=0.002)$ and gram intake of low fat items was significantly greater than intake of high fat items $(t(57)=9.520, p<0.001)$.

There was a significant reduction in HFSV intake with inulin fiber and ZOTRIM combined compared to placebo $(t(57)=4.315, p<0.001)$ and compared to inulin fiber alone $(t(57)=3.127, p=0.003)$. For LFSV intake, there was a significant reduction with ZOTRIM alone $(t(57)=2.593, p=0.012)$ and with the ZOTRIM and inulin fiber combination $(t(57)=2.470, p=0.017)$ compared to placebo. Intake of LFSV items was also significantly reduced following ZOTRIM alone $(t(57)=2.004, p=0.050)$ and ZOTRIM+inulin fiber combined $(t(57)=2.036, p=0.046)$ compared to inulin fiber alone.

It was also found that gram intake of HFSW items was significantly reduced with ZOTRIM alone $(t(57)=2.207, p=0.031)$ and with ZOTRIM+inulin fiber combined $(t(57)=5.099, p<0.001)$ compared to placebo. HFSW intake was also significantly lower with ZOTRIM+inulin fiber combined versus with ZOTRIM alone $(t(57)=2.440, p=0.018)$ or inulin fiber alone (t (57)=3.146, p=0.003). No significant effects of ZOTRIM or inulin fiber were found on gram intake of LFSW items.

Total Daily Intake. Total daily intake, including calories from the product, breakfast and lunch was analyzed using a 2×2 repeated measures ANOVA. This demonstrated a main effect of ZOTRIM on kcal intake (F (1,57)=16.681, p<0.001). There was no effect of inulin fiber (F (1,57)=1.880, p=0.176) and no interaction between inulin fiber and ZOTRIM (F (1,57), =0.193, p=0.662). Paired t-tests revealed that there was a significant reduction in kcal intake with ZOTRIM alone (t (57)=3.365, p=0.001) and with the inulin fiber and ZOTRIM combination (t (57)=4.238, p<0.001) compared to placebo. It was also found that the kcal intake after ZOTRIM alone (t (57)=2.417, p=0.019) and after the combination of inulin fiber and ZOTRIM (t (57)=3.178, p=0.002) was less than with inulin fiber alone.

Appetite. Subjective parameters (hunger, gastric fullness, satisfaction, desire to eat, prospective consumption, thirst and nausea) rated on VAS were analyzed using within-subject ANOVA for repeated measures with condition and time as within-subjects factors. Main effects of time were observed, as expected, reflecting changes in appetite ratings during the study days. Trends for main effects of hunger and desire to eat were observed as well as a main effect for nausea.

Trend for a main effect of ZOTRIM on hunger ratings (F(1, 56)=2.865, p=0.096). T-tests were used to investigate where the significant differences lay and showed that compared to the control condition a significant reduction in ratings of hunger was found in the ZOTRIM and inulin fiber combined condition at the pre lunch time point, (t(57)=2.071, p=0.043), mean values: 61.02 mm versus 54.41 mm respectively). Furthermore, compared to the inulin fiber only condition a significant reduction in ratings of hunger was found in the ZOTRIM and inulin fiber combined condition at the post lunch time point, (t(57)=2.770, p=0.008, mean values: 7.73 mm and 4.71 mm respectively).

Trend for an interaction between fiber and time on desire to eat (F(8, 456)=1.870, p=0.063). T-tests were used to investigate where the significant differences lay and showed that, compared to the control condition, a significant reduction in ratings of desire to eat was found in the ZOTRIM and inulin fiber combined condition at the pre dose lunch time point, (t(57)=2.302, p=0.025, mean values=: 58.84 mm versus 51.29 mm respectively). Furthermore, compared to the control condition a significant reduction in ratings of desire to eat was found in the inulin fiber only condition at the pre lunch time point, (t(57)=2.011, p=0.049, mean values: 61.19 mm versus 55.26 mm respectively). Moreover, compared to the control condition a significant reduction in ratings of desire to eat was found in the ZOTRIM and inulin fiber combined condition at the pre lunch time point, (t(57)=2.230, p=0.030, mean values: 61.19 mm versus 53.86 mm respectively).

Significant main effect of fiber on nausea (F(1, 55)=6.203, p=0.016). T-tests were used to investigate where the significant differences lay and showed that compared to the control condition a significant reduction in ratings of nausea was found in the inulin fiber only condition 2 hours after breakfast time point, (t(57)=2.390, p=0.020, mean values: 9.50 mm versus 5.69 mm respectively). Furthermore, compared to the ZOTRIM only condition there was a significant reduction in nausea in the inulin fiber only condition at the 2 hours after breakfast time point, (t(57)=2.584, p=0.012, mean values: 10.03 mm versus 5.69 mm respectively). Furthermore, compared to the ZOTRIM and inulin combined condition there was a significant reduction in the inulin fiber only condition in ratings of nausea at the 2 hours after breakfast time point, (t(57)=2.053, p=0.045, mean values: 7.60 mm versus 5.69 mm respectively). Moreover, compared to the ZOTRIM only condition there was a significant reduction in ratings of nausea in the inulin fiber only condition at the pre dose lunch time point, (t(57)=2.040, p=0.046, mean values: 8.88 mm versus 5.97 mm respectively). In addition, compared to the ZOTRIM only condition there was a significant reduction in ratings of nausea in ZOTRIM and inulin fiber combined at the pre dose lunch time point, (t(57)=2.407, p=0.019, mean values: 8.88 mm versus 6.00 mm respectively).

EXAMPLE 3

Animal Model for Food Intake

Studies are conducted with male Sprague-Dawley rats weighing 270-290 grams. Three days before the start of an experiment, the animals are weighed and individually housed. Normal rat chow pellets and tap water are present ad libitum and are provided by food troughs and drinking spouts, which allow continuous recording of the food consumed. Compositions containing plant extracts+inulin are administered at predetermined times to the treatment group. Food intake is recorded by continuously weighing the amount of food remaining in a round stainless steel food basket. Food intake is continuously or intermittently recorded over the entire time of an experiment. The weight of each animal is determined on each day of the experiment and recorded, together with any unusual observations, e.g., stressed animals, difficulties with plant extract application, etc. Statistical analysis to detect differences in ingestive behavior between the control group and the treatment group is performed.

What is claimed is:

1. A method for reducing food intake in a human in need thereof consisting essentially of administering to said human prior to food intake a composition that reduces food intake by 20 to 40% in the human compared to a human not administered said composition, wherein said composition consists essentially of therapeutically effective amounts of guarana seed extract, damiana leaf extract and yerbe mate leaf extract, and therapeutically effective amounts of an isolated fermentable dietary fiber selected from the group consisting of inulin, a beta glucan, pectin, natural gum, oligosaccharide, psyllium seed husk, a resistant dextrin and combinations thereof.

2. The method of claim 1, wherein the composition reduces food intake by 20 to 30% in the human.

3. The method of claim 1, wherein the composition reduces calorie intake by 10 to 35% in the human.

4. The method of claim 1, wherein the human has a body mass index in the range of 18.5 to 29.9 kg/m$^2$.

5. The method of claim 1, wherein the human has a body mass index of greater than 29.9 kg/m$^2$.

* * * * *